(12) United States Patent
Kovacs et al.

(10) Patent No.: US 6,852,854 B1
(45) Date of Patent: Feb. 8, 2005

(54) PREFORMED CARBOXYLATED ACTIVE ESTER FOR LABELING BIOMOLECULES

(75) Inventors: Zoltan Kovacs, Lewisville, TX (US); Dhurjati S. Mudigonda, Plano, TX (US); A. Dean Sherry, Dallas, TX (US)

(73) Assignee: PsiloQuest Inc., Orlando, FL (US)

( * ) Notice: Subject to any disclaimer, the term of this patent is extended or adjusted under 35 U.S.C. 154(b) by 28 days.

(21) Appl. No.: 10/262,454

(22) Filed: Oct. 1, 2002

(51) Int. Cl.$^7$ .................. C07D 295/23; C07F 19/00
(52) U.S. Cl. ................. 540/474; 540/470; 540/476; 549/470; 534/10
(58) Field of Search .................. 540/470, 474, 540/476; 534/10, 14, 15, 16; 548/523, 524; 514/318, 185; 544/64; 549/470

(56) References Cited

U.S. PATENT DOCUMENTS

| | | | |
|---|---|---|---|
| 5,428,156 A | | 6/1995 | Mease et al. |
| 5,565,562 A | * | 10/1996 | Parker et al. ............... 540/465 |
| 5,573,752 A | * | 11/1996 | Ranganathan et al. ... 424/9.363 |
| 5,639,879 A | | 6/1997 | Mease et al. |
| 5,962,679 A | | 10/1999 | Ripa et al. |

OTHER PUBLICATIONS

Louis A. Carpino, Hideko Imazumi, Ayman El–Faham, Fernando J, Ferrer, Chongwu Zhang, Yunsub Lee, Bruce M. Foxman, Peter Henklein, Christiane Hanay, Clements Mugge, Holger Wenschub, Jans Klose, Michael Beyermann and Michael Bienert; "The Urunium/Guanidinium Peptide Coupling Reagents: Finally the True Urunium Salts"; Angew. Chem, Int. Ed. 2002, 41, No. 3; pp. 442–445.

Larry Yet; "Peptide Coupling Reagents: Names, Acronyms and References"; Albany Molecular Research, Inc., Technical Reports, vol., 4, No. 1, pp. 1999; pp. 1–7.

Yasushi Arano, et al.: "Conventional and High–Yield Synthesis of DTPA–Conjugated Peptides: Application of a Monoreactive DTPA to DTPA–D–Phe1–octreotide Synthesis"; 1997 American Chemical Society, Bioconjugate Chem. 1997, 8, pp. 442–446.

Yasushi Arano, et al.; "Reassessment of Diethylenetriaminepentaacetic Acid (DTPA) as a Chelating Agent for Indium–111 Labeling of Polypeptides Using a Newly Synthesized Monoreactive DTPA Derivative"; 1996 American Chemical Society, J. Med. Chem. 1996, 39, pp. 3451–3460.

* cited by examiner

*Primary Examiner*—James Wilson
*Assistant Examiner*—Ganapathy Krishnan

(57) ABSTRACT

The present invention is directed, in general, to a method for making high yields of functionalized cyclic or acyclic tertiary amine-containing compounds, termed active esters, the functionalized compounds themselves, and diagnostic or therapeutic systems incorporating such compounds. Ester groups are attached to all but one of its Nitrogen atoms of the tertiary amine-containing compound. Therefore, an active agent, in the presence of coupling agent, attaches to the remaining amine via a carboxylate group attached to the amine, to produce high yields of the active ester. The active ester is then combined with a biomolecule, to produce high yields of a bioconjugated product. A metal ion may be chelated to the bioconjugated product to produce a chelating agent for use in either diagnostic or therapeutic applications.

4 Claims, No Drawings

PREFORMED CARBOXYLATED ACTIVE ESTER FOR LABELING BIOMOLECULES

CROSS-REFERENCE TO RELATED APPLICATIONS

This application is related to the disclosures of U.S. application Ser. Nos.: 101262.388, entitled, "IMPROVED PROCESS FOR MAKING A CHELATING AGENT FOR LABELING BIOMOLECULES USING PREFORMED ACTIVE ESTERS;" 10/262.340, entitled, "A PRE-FORMED ACTIVE ESTER FOR LABELRNG BIOMOL-ECULES;" 10/262,335, entitled, "A CHELATING AGENT USING PREFORMED ACTIVE ESTERS FOR LABEL-ING BIOMOLECULES;" 10/262.392, entitled, "A DIAG-NOSTIC SYSTEM USING LABELED BIOMOLECULES THAT CONTAIN A CHELATING AGENT FORMED WITH PREFORMED ACTIVE ESTERS;" 10/262,450, entitled, "A THERAPEUTIC SYSTEM USING LABELED BIOMOLECULES THAT CONTAIN A CHELATING AGENT FORMED WITH PREFORMED ACTIVE ESTERS;" all to Zoltan Kovacs; Dhurjati S. Mudigonda; and A. Dean Sherry, all filed on Oct. 1, 2002, commonly assigned with the present invention, and incorporated by reference as if reproduced herein in their entirety.

TECHNICAL FIELD OF THE INVENTION

The present invention is directed to chelating agents, a method for preparing chelating agents and methods of using chelating agents in diagnostic and therapeutic applications, and more particularly, to the labeling of biomolecules using activated esters of tertiary amines having high affinity for metal ions.

BACKGROUND OF THE INVENTION

The ability of certain amine-containing macrocyclic compounds, or their acyclic equivalents, to tightly bind metal ions makes these compounds attractive choices as metal ion chelating agents for use in medical diagnosis or therapy. To facilitate diagnosis or therapy, it is desirable to covalently attach, or conjugate, the metal ion-chelating agent complex to biomolecules, such as antibodies. One method of achieving conjugation to a biomolecule is by introducing an active group into the chelating agent and then reacting the active group with a functional group on the biomolecule. For example, the chelating agent may be functionalized with an active group, such as N-hydroxy succinimide (NHS), that in turn, can react with a functional group on the biomolecule.

There is a longstanding need for the efficient preparation of functionalized chelating agents with active groups that can couple the-chelating agent to biomolecules. For example, the efficient functionalization of macrocyclic compounds, such as 1,4,7,10-tetraazocyclododecane-1,4,7,10 tetraacetic acid (DOTA) and 1,4,8,11-tetraazocyclotetradecane 1,4,8,11-tetraacetic acid (TETA), remains problematic. As discussed in U.S. Pat. Nos. 5,428, 156 and 5,639,879 to Mease et al., incorporated herein by reference, previous methods for the preparation of function-alized DOTA or TETA are complex, and may yield mixed anhydride products that are highly sensitive to hydrolysis in water, or products with greater than one active ester attached to the chelating agent. The latter can result in the undesirable crosslinking of two or more biomolecules via a reaction between biomolecules and the active esters attached to a single chelating agent.

In an attempt to address these problems, Mease et al., proposed a method to produce DOTA-NHS and TETA-NHS. Mease et al. starts with commercially available 1,4, 7,10-tetraazacyclododecane (Cyclen) (or 1,4,8,11-tetraazacyclotetradecane; Cyclam), which is cyanomethylated to produce a tetranitrile. The tetranitrile is then hydrolyzed and acidified to produce DOTA. DOTA has four equivalent free carboxylate groups (i.e., four acetate groups) attached to the Nitrogen atoms of the 1,4,7,10-tetraazacyclododecane ring. To make DOTA-NHS, Mease et al. then prepared a mixture of DOTA, NHS, and a coupling agent, dicyclohexylcarbodiimide (DCC), using dimethylsul-foxide as the solvent. Mease et al., then reacts this product mixture with a biomolecule to make a DOTA-biomolecule conjugation product. There are several problems with this approach, however.

First, the production of mono-substituted DOTA-NHS may be less than desired. This is expected because all four carboxylate groups of DOTA are available for derivatization, and therefore there is no control over the number or location of N-hydroxysuccinimidyl esters attached to DOTA. It is expected, for example, that if equi-molar amounts of DOTA, NHS and DCC were reacted, then a substantial proportion of di-, tri- and tetra-NHS substituted DOTA compound would be present in the product mixture. To reduce the production of such multi-substituted DOTA-NHS compounds, Mease et al. reacted one molar equivalent of DOTA with 0.5 molar equivalents of DCC and NHS. By doing so, Mease et al. found an average of one carboxylic acid on DOTA reacted with NHS. This approach however, must result in low yields of DOTA-NHS. Specifically, if 1 mole of DOTA is reacted with 0.5 moles of NHS, it follows therefore, that the yield of DOTA-NHS could not exceed 50 mole percent. Moreover, this is not an isolated yield of pure DOTA-NHS.

This raises a second problem. Because NHS-substituted DOTA compounds contain a highly reactive Oxygen-Nitrogen bond that links DOTA to NHS, it would be difficult to isolate mono-substituted DOTA-NHS from a mixture of di-, tri- and tetra-NHS substituted DOTA compounds. It is also expected that standard isolation techniques would cause substantial hydrolysis of mono-substituted DOTA-NHS back to the starting compounds. Alternatively, the use of unpurified mixtures of mono-, di-, tri- and tetra-NHS sub-stituted DOTA is expected to resul in poor yields of DOTA bioconjugated to biomolecules in useful fashion.

A third problem associated with the use of multi-NHS substituted DOTA is the potential of crosslinking two or more biomolecules to each other when more than one biomolecule conjugates to a single DOTA molecule. Such cross-linked biomolecule-DOTA conjugates may have poor uptake to a target location, such as a specific organ or cell types, when delivered to a living system.

There is a fourth problem related to the stability of NHS substituted DOTA. The ester group in NHS-substituted DOTA is highly susceptible to hydrolysis in the presence of water. Therefore, even small amounts of water present or absorbed into the dimethylsulfoxide solvent used by Mease et al. will result in hydrolysis of mono-NHS substituted DOTA, thereby reducing the total amount of NHS substi-tuted DOTA available to react with biomolecules.

Accordingly, what is needed is an improved process for the efficient manufacture of functionalized chelating agent that avoids the problems encountered in previous processes.

SUMMARY OF THE INVENTION

To address the deficiencies of the prior art, the present invention, in one embodiment, a carboxylated active ester. The carboxylated active ester comprises a tertiary amine where said tertiary amine is cyclic or acyclic having the general formula:

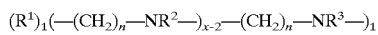

where n is 2 or 3. X is 3 or 6 and $R^1$ is$((CH_2)_n-NR^2-)$, when the tertiary amine is cyclic, or x is 3, 4 or 6 and $R^1$ is $NR^2-$, when the tertiary amine is acyclic. $R^2$ includes a carboxylic acid group and $R^3$ includes an ester group.

Yet another embodiment is a carboxylated active ester produced by a process. The process comprises providing a tertiary amine where said tertiary amine is cyclic or acyclic having the general formula:

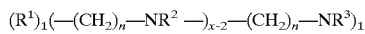

where n is 2 or 3 and x is 3, 4 or 6. $R^1$ is $((CH_2)_n-NR^2-)$, when the tertiary amine is cyclic, or $R^1$ is $NR^2-$ when the tertiary amine is acyclic. $R^2$ includes a first ester group; and $R^3$ includes a carboxylic acid group. The process further includes combining the tertiary amine with a coupling agent and an active compound to convert the $R^3$ to a second ester group to thereby form an active ester. The process also includes cleaving the $R^2$ groups of the active ester to thereby form the carboxylated active ester.

The foregoing has outlined, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the scope of the invention.

DETAILED DESCRIPTION

The present invention is directed to a process for the production of high yields of functionalized cyclic or acyclic tertiary amine-containing compounds (referred to throughout as tertiary amines) that, in turn, are used to label bimolecules for diagnostic or therapeutic applications. The functionalized cyclic or acyclic tertiary amines are termed active ester or carboxylated active esters. The term active ester as used herein, refers to any ester-containing compound capable of reacting with functional groups, such as an amine or sulfhydryl groups, in a biomolecule. The term carboxylated active ester as used herein, refers to an active ester having free carboxylic acid groups attached to Nitrogen atoms in the tertiary amine.

Because all but one of the Nitrogen atoms in the tertiary amines have a first ester group attached thereto, an active agent, in the presence of a coupling agent, attaches to the remaining amine that has a carboxylate group attached thereto, to produce high yields of an active ester having a second ester group. The first ester groups in the active ester may be cleaved to yield a carboxylated active ester. In the cleavage environment, the second ester, associated with the attached active agent, is not cleaved, resulting in high isolated yields of a carboxylated active ester.

This process conveniently offers greater control on the preparation of bioconjugated products by virtue of providing stable and pure compounds for functionalizing biomolecules. When either the active ester or carboxylated active ester are combined with a biomolecule, high yields of a bioconjugated product are formed. The term bionconjugated product as used herein, refers to a chemical compound that has been formed by the joining of one or more organic compounds containing an active ester to a biomolecule. A metal ion may be chelated to the bioconjugated product to produce a chelating agent, for use in either diagnostic or therapeutic applications.

One particular embodiment of the present invention is directed to a process for making a chelating agent. The process comprises providing a tertiary amine where the tertiary amine is cyclic or acyclic having the general formula:

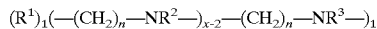

where n is 2 or 3 and x is 3, 4 or 6. $R^1$ is $((CH_2)^n-NR^2-)_1$ when the tertiary amine is cyclic, or $R^1$ is $NR^2-$ when the tertiary amine is acyclic. $R^2$ includes a first ester group and $R^3$ includes a carboxylic acid group. The process includes combining the tertiary amine with a coupling agent and an active compound to convert the $R^3$ to a second ester group and thereby form an active ester. The process further includes combining the active ester with a biomolecule to form a bioconjugated product and chelating a metal ion to the bioconjugated product.

The tertiary amine may be any cyclic or acyclic organic compound contang a tertiary amine and having the above-described general formula. Preferred embodiments of cyclic tertiary amines are triazacyclononanes, tetraazacyclododecanes, and hexaazacyclooctodecanes. In such embodiments the carboxylic acid group is coupled to any one Nitrogen atom in the cyclic compound and the first ester group is coupled to remaining Nitrogen atoms in the cyclic compound. More preferably, the tertiary amine is selected from a group of cyclic compounds consisting of: 1,4,7, triazcyclononane 1,4 diester 7 monocaboxylate; 1,4, 7,10 tetraazacyclododecane 1,4,7 triester 10 monocarboxylate; and 1,4,7,10,13,16 hexaazacyclooctadecane 1,4,7,10, 13 pentaester 16 monocarboxylate. In these embodiments, the di-, tri- and pentaester comprise the first ester group and the monocarboxylate comprises said carboxylic acid group. Even more preferably the first ester group is tertiary butyl ester and the carboxylic acid group is acetate.

Preferred embodiments of acyclic tertiary amines are diethyltriamines, triethyltetraamines, and pentaethylhexaamines. In such embodiments, the carboxyl group is coupled to any one Nitrogen atom in the acyclic compound and the first ester group is coupled to remaining Nitrogen atoms in the acyclic compound. More preferred embodiments are: diethyltriamine 1,7 diester 4 monocarboxylate; triethyltetraamine 1,4,10 triester 7 monocarboxylate; and pentaethylhexaamine 1,4,7,13,16 pentaester 10 monocarboxylate. Analogous to the cyclic compounds, the di-, tri- and pentaester comprise the first ester group and the monocarboxylate comprises said carboxylic acid group. Also similar to the cyclic compounds preferably, the ester group is tertiary butyl ester and the carboxylic acid group is acetate.

Any conventional process may be used to selectively attach the $R^2$ group including the first ester to Nitrogen atoms of the tertiary amine. For example, the synthesis of polyazamacrocyles having pendent arms comprising organic substitutants has been described in: U.S. Pat. No. 5,428,155, to Sherry A. D. and van Westrenen, J.; Kovacs and Sherry, *pH-Controlled Selective Protection of Polyaza Macrocycles,* SYNTHESIS, 761–63, (July 1997); Zhang S., Wu. K., Biewer M. C., & Sherry A. D. *$^1H$ and $^{17}O$ NMR Detection of a Lanthanide-Bound Water Molecule at Ambient Tempera-*

*tures in Pure Water*, 40 INORG. CHEM. 4284–90 (2001); which are all incorporated herein by reference.

Alternatively, such compounds are commercially available. It is preferable to remove salts, such as HBr from the tertiary amine using conventional processes, such as column chromatography or recrystallization.

The $R^2$ group may comprise any conventional functional group that is capable of preventing the coupling of NHS to the ester group of $R^2$ in the presence of the coupling agent. It is also preferable that $R^2$ does not contain any functional groups capable of reacting with either the active compound, such as NHS, or the coupling agent. In certain preferred embodiments, carboxylate groups attached to the Nitrogen atoms of the tertiary amine may be selectively alkylated to provide esters having alkyl, cycloalkyl or aromatic groups attached thereto. More preferably, the $R^2$ group has the general formula:

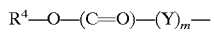

$$R^4\!-\!O\!-\!(C\!=\!O)\!-\!(Y)_m\!-\!$$

where m is between 0 and 20, Y is a branched or linear organic substituent and $R^4$ includes an organic substituent. Preferable $R^4$ is selected from a group consisting of: Alkyl groups having 20 carbon atoms or less; Cycloalkyl groups having 20 carbon atoms or less; and Aromatic groups having 20 carbon atoms or less.

The term organic substituent as used herein refers to any carbon-containing compound. In certain preferred embodiments, Y is an alkyl group. $R^4$ may be any compound containing the ester and that does not react with the active compound. $R^4$ is preferably capable of being removed in the presence of an anhydrous acid environment, as further discussed below. In certain preferred embodiments, for example, $R^4$ comprises a tertiary butyl group such as $(CH_3)_3\!-\!C\!-\!$, Y is $CH_2$ and m is 1. In other preferred embodiments, $R^4$ comprises 2,2,2 bicyclohexane. In still other preferred embodiments, $R^4$ comprises substituted or unsubstituted Adamantyl groups.

The coupling agent may comprise any conventional compound known by those skilled in the art to facilitate the coupling of the active compound, such as NHS, to the carboxylate group of R3. In particular, peptide coupling agents, such as those described in Larry Yet, Peptide Coupling Reagent: *Names, Acronyms and References*, ALBANY MOLECULAR RESERCH, INC. TECHNICAL REPORT, VOL. 4 NUMBER 1 (1999); or in Louis A. Carpino et al., *The Uronium/Guanidium Peptide Coupling Reagents: Finally the True Uronium Salts*, ANGEW. CHEM INT. ED. 41, 441 (2002), both incorporated by reference herein, may be used. Such compounds are well known to those skilled in the art and may include carbodiimides, such as 1,3-diccyclohexylcarbodiimides (DCC).

More preferably, however the coupling agent is an aminium, guanidium or uronium-containing compound. In certain preferred embodiments, for example, the coupling agent is 2—(1H-Benzotriazole-1—yl)-1,1,3,3-tetramethyluronium hexafluorophosphate (HBTU) in either the N-form or O-form, and more preferably the more reactive O-form. The terms N-form and O-form as used herein, refer to the atoms, either nitrogen or oxygen, directly involved in forming the covalent linkage between the benzotriazole group and the tetramethyluronium group. Such compounds are available from commercial suppliers, such Calbiochem-Novabiochem GmbH (Germany).

The active compound may be any compound capable of attaching to, and thereby converting, the carboxyl group of $R^3$ to an ester. Moreover, the active compound is selected such that the resulting second ester attached to the $R^3$ group, while capable of reacting with sulfhydryl, and more preferably, amine group during bioconjugation, is not cleaved substantially by acids in an aprotic solvent. Preferred classes of active compound include: imide-containing compounds; Aryl-containing compounds substituted with electron withdrawing groups, such as halogen, nitrile or cyanide; or triazol-containing compounds. In certain preferred embodiments, for example, the active compound is an imide, such as N-hydroxy succinimide (NHS). In other preferred embodiments, the active compound is an aryl-containing compounds comprising pentafluoro phenyl. In other preferred embodiments, the active compound is triazol-containing compound comprising 1-Hydroxybenzotriazole.

Preferably, the tertiary amine, coupling agent and active compound are combined in a solvent capable of dissolving these compounds to form a homogenous mixture. It is advantageous for the solvent is to be an aprotic organic solvent, such as dimethylformamide and, more preferably, acetonitrile. Preferably, the molar ratio tertiary amine, coupling agent and active compound in the mixture is about 1:1.05:1.05. Typically, the concentration of tertiary amine in the mixture is about 1 Molar. The reaction is preferably carried out by maintaining a solution containing the tertiary amine, coupling agent and active compound at a constant temperature with stirring for about 2 to about 24 hours to allow the formation of the active ester. The reaction may be carried out at any temperature where the mixture remains in a liquid state; preferably from about 10° to about 50° C., more preferably from about 0 to about 30° C., and even more preferably at room temperature.

After the reaction period, the organic solvent is removed by conventional techniques, such as vacuum evaporation using a rotary evaporator at about 40° C. The residual solid comprising the active ester is then dissolved in a first wash solvent, such as dichloromethane, and optionally washed multiple times with a second wash solvent that is immiscible with the first wash solvent, such as water. The washing solvents are preferably prechilled to less than room temperature, and more preferably less than about 4° C. The washing steps are preferably carried out in a vessel, such as a separatory funnel, to facilitate removal of the second wash solvent.

Next, the first wash solvent containing the active ester is transferred to another vessel. A hydroscopic salt, such as sodium sulfate is added to the vessel to remove residual water. The vessel is then cooled to about 4° C. for about 15 minutes, after which the mixture is filtered, for example, in a sintered glass filter. The first wash solvent is then removed from the filtrate, for example, using vacuum evaporation.

The residual solid comprising the active ester may then be further purified by redissolving the solid in a third organic solvent, such as anhydrous ethyl acetate, at about 40° C. and then allowed to recrystallize at about 4° C. The third organic solvent is then removed from the white solid crystals comprising the active ester via filtration.

In certain preferred embodiments of the process, the isolated yield of the active ester is greater than about 50 mole percent (percent calculated based on moles of active ester formed per mole of tertiary amine in the starting materials), more preferably greater than about 70 mole percent and even more preferably greater than about 80 mole percent.

The term isolated yield as used herein refers to the amount of a purified stable active ester, or carboxlylated active ester as described below, obtained from a known amount of tertiary amine. The term purified as used herein means that at least about 95 wt % of the solid obtained from the above described process comprises the active ester or its salts.

In certain embodiments, the active ester may be combined with the biomolecule in the presence of a protic solvent, such as water, to form the bioconjugated product. It may be advantageous, however, for the active ester to be converted to a carboxylated active ester, before being combined with the biomolecule. This follows because the structure of certain biomolecules may be irreversibly altered the presence of, for example, a strong acid used to facilitate cleavage. In such instances, the process therefore further includes cleaving the $R^2$ groups of the active ester in the presence of an acid to form a carboxylated active ester.

In certain applications it may advantageous to produce bulk quantities of the active ester, such as tertiary butyl-substituted DOTA-NHS, because this compound is more stable than the carboxylated active ester, such as DOTA-NHS. It is thought that the ester groups in $R^2$ help stabilize the active ester against hydrolysis in the presence of water or other protic solvents. While not limiting the scope of the present invention by theory, it is believed that active esters containing bulky hydrophobic groups, such as tertiary butyl groups, are better able to exclude water as compared to the carboxylated active ester, and thereby reduce the rate of hydrolysis of the active ester. In certain embodiments, for example, the half-life of the active ester in water at room temperature and neutral or acidic pH is expected to be five to seven times longer than the half-life of the carboxylated active ester, which is about 10 and preferably at least about 20 minutes.

To form a carboxylated active ester from the active ester, the $R^2$ groups are cleaved in the presence of an acid. To minimize the hydrolysis of the ester in the $R^3$ group, the cleavage reaction is preferably carried out in a substantially aprotic solvent. To facilitate its removal, the acid used to facilitate cleavage is preferably a volatile acid.

In certain embodiments, for example, the active ester is dissolved or suspended in a first organic solvent, such as dichloromethane. Preferably a volatile acid, such as gaseous HCl, or more preferably, trifluoroacetic acid, is added to the dissolved or suspended active ester. Cleavage of the ester group in $R^2$ is allowed to proceed for a sufficient period to ensure substantially complete conversion to carboxylic acid groups. The reaction is carried out for a period and temperature range similar to that described for preparing the active ester. Typical reaction conditions are room temperature for at least about 2 hours and preferably at least about 12 hours.

After the cleavage of the ester group in $R^2$ is substantially complete, the acid and the first organic solvent are removed, for example by, vacuum evaporation. The residual solid, comprising the carboxylated active ester, may optionally be further purified by repeatedly washing the solid in a second organic solvent, such as diethyl ether, and decanting the solvent from the resulting white solid comprising the carboxylated active ester. The white solid may be dried, and the second organic solvent more fully removed, by conventional vacuum evaporation, preferably using a vacuum of less than about 0.1 Torr. In certain preferred embodiments of the process, the isolated yield of the carboxylated active ester from the active ester is at least about 90 mole percent and preferably greater than 95 mole percent.

The active ester or carboxylated active ester may then be combined with biomolecules, using conventional processes, to form high yields of a bioconjugated product. For example, U.S. Pat. No. 5,639,879 to Mease et al., incorporated by reference herein, discusses the bioconjugation of 1,4,7,10-tetraazacyclododecane-1,4,7,10-tetra(aceticacid)-10-mono (N-hydroxysuccinimidyl ester) (DOTA-NHS) to monoclonal antibodies.

The biomolecule may comprise, for example, biopolymers comprised of amino acid sequences, such as, proteins, such as immunoglobins, peptides, nucleic acid sequences, such as DNA, RNA or oligonuceotides, or carbohydrate, such as oligosaccharides or polysaccharides, or combinations thereof (e.g., proteins have carbohydrate molecules attached thereto). or other biochemicals well known to those of ordinary skill in the art.

It is expected that preparing and purifying the active ester or carboxylated active ester according to the present invention results in a high yield of the bioconjugated product, for example, greater than about 30 and more preferably 95 mole percent. Bioconjugation is preferably carried out at a pH between about 6.0 and about 9.0, as maintained by a conventional buffer, such as phosphate buffer. R3 includes a linking group, when covalently attached to the biomolecule. In certain embodiments, the linking group comprises a thioester, and more preferably an amide.

In embodiments where the active ester is conjugated to the biomolecule, an acid may be mixed with the bioconjugated product to facilitate cleavage of the ester group in $R^2$ for a sufficient period to ensure substantially complete conversion to carboxylic acid groups, to produce the same bioconjugated product as described above.

The bioconjugated product may then be combined with metal ions to form the chelating agent. For example, a metal ion salt, preferably the chloride salt, is dissolved in water and added to the bioconjugated product. The pH range of solution is preferably between about 5 and about 9. The mixture is stirred for a sufficient period to ensure chelation of the metal ion to the bioconjugated product, for example, between about 30 minutes and about 12 hours. The resulting chelating agent-containing solution is then filtered and subjected to further purification procedures, such as dialysis or gel filtration.

The metal ion is preferably a divalent, trivalent or tetravalent cation having a high affinity for the bioconjugated product. It is desirable, for example, for the stability constant (log Ka) of the metal ion to the bioconjugated product to be at least 12, preferably greater than 16, and more preferably greater than 20. Moreover, in certain embodiments the metal ion binds to the bioconjugated product rapidly. For instance, when the tertiary amine is an acyclic compound, a substantial proportion, for example, greater than 50 percent and more preferably greater than 90 percent, of the metal ion is expected to bind to the bioconjugated product within 30 minutes, and more preferably within 5 minutes.

The choice of metal ion used to form the chelating agent depends on the anticipated diagnostic or therapeutic application for the chelating agent. For example, for Magnetic Resonance imaging diagnostic applications, preferred metal ions include: $Gd^{3+}$, $Eu^{3+}$, $Tm^{3+}$, $Mn^{2+}$ and $Dy^{3+}$. Alternatively, for diagnostic applications based on measuring radioactivity, preferred metal ions include: $^{111}In^{3+}$, $^{113m}In^{3+}$, $^{115}In^{3+}$, $^{67}Ga^{3+}$, $^{68}Ga^{3+}$, $Tl^{3+}$ and $^{99m}TC^{4+}$. Or, for radiotherapeutic applications based on the targeted delivery of radioactivity emitted by a metal ion, the preferred metal ions include: $^{153}Sm^{3+}$, $^{166}Ho^{3+}$, and $^{212}Bi^{3+}$, and more preferably, $^{90}Y^{3+}$, $^{117}Lu^{3+}$ and $^{225}Ac^{3+}$. Other metal ions for radiodiagnostic or radiotherapeutic applications include: $^{149}Pm$, $^{159}Gd$, $^{140}La$, $^{175}Yb$, $^{47}SC$, $^{186}Re$, $^{188}Re$, $^{97}Ru$, $^{105}Rh$, $^{109}Pd$, $^{197}Pt$, $^{67}Cu$, $^{198}Au$, $^{117}Sn$, and $^{212}Pb$.

Another aspect of the present invention is directed to embodiments of a carboxylated active ester. The carboxylated active ester comprises a tertiary amine where said tertiary amine is, cyclic or acyclic having the general formula:

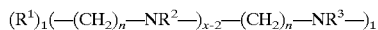

where n is 2 or 3. X is 3 or 6 and $R^1$ is $((CH_2)_n\text{—}NR^2\text{—})$, when the tertiary amine is cyclic, or x is 3, 4 or 6 and $R^1$ is $NR^2\text{—}$, when the tertiary amine is acyclic. $R^2$ includes a carboxylic acid group and $R^3$ includes an ester group.

In certain preferred embodimnets of carboxylated active ester tertiary amine is selected from a group of cyclic compounds consistig of: triazcyclononanes and hexazacyclooctadecanes. In such embodiments, the ester group is coupled to any one Nitrogen atom in the cyclic compounds and the carboxylic acid group is coupled to remaining Nitrogen atoms in the cyclic compounds. In other preferred embodiments, tertiary amine is selected from a group of cyclic compounds consisting of: 1,4,7, tiazacyclononane 1,4 dicarboxylate 7 monoester; and 1,4,7,10,13,16 hexaazacyclooctadecane 1,4,7,10,13 pentacatboxylate 16 monoester. In such embodiments, the di- and pentacarboxylate comprise the carboxylic acid group in the $R^2$ and the monoester group comprises the ester group in the $R^3$. In certain embodiments, for example, carboxylic acid in said $R^3$ is acetate and said ester group in said $R^3$ includes N-hydroxy succinimide. In yet other preferred embodiments of the carboxylated active ester, the tertiary amine is selected from a group of acyclic compounds consisting of: diethyltriamines; triethyltetraamines; and pentaethylhexaamines. In such embodiments the ester group is coupled to any one Nitrogen atom in the acyclic compounds and the carboxylic acid group is coupled to remaining Nitrogen atoms in the acyclic compounds. In yet other preferred embodiments, the tertiary amine is selected from a group of acyclic compounds consisting of: triethyltetraamine 1,4,10 tricarboxylate 7 monoester; and pentaethylhexaamine 1,4,7,13,16 pentacarboxylate monoester. In such embodiments, the di-, tri- and pentacarboxylate comprise the carboxylic acid group in the $R^2$ and the monoester comprises the ester group in the $R^3$.

In still other embodiments of the carboxylated active ester $R^2$ group has the general formula $R^4\text{—}O\text{—}(C\text{=}O)\text{—}(Y)_m\text{—}$ where m is between 0 and 20, Y is a branched or linear organic substituent. In such embodiments, $R^4$ includes an organic substituent and the $R^4$ is selected from the group consisting of: Alkyl groups having 20 carbon atoms or less; Cycloalkyl groups having 20 carbon atoms or less; and Aromatic groups having 20 carbon atoms or less.

Yet another embodiment is a carboxylated active ester produced by a process. The process comprises providing a tertiary amine where said tertiary amine is cyclic or acyclic having the general formula:

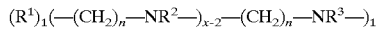

where n is 2 or 3 and x is 3, 4 or 6. $R^1$ is$((CH_2)_n\text{—}NR^2)_1$ when the tertiary amine is cyclic, or $R^1$ is $NR^2\text{—}$ when the tertiary amine is acyclic. $R^2$ includes a first ester group; and $R^3$ includes a carboxylic acid group. The process further includes combining the tertiary amine with a coupling agent and an active compound to convert the $R^3$ to a second ester group to thereby form an active ester. The process also includes cleaving the $R^2$ groups of the active ester to thereby form the carboxylated active ester.

In certain preferred embodiment of the carboxylate dactive ester produced by the above-described process, tertiary amine is selected from a group of cyclic compounds consisting of: triazaccyclononanes, tetraazacyclododecanes; and hexaazacyclooctadecanes. In such embodiments, the carboxylic acid group is coupled to any one Nitrogen atom in the cyclic compounds and the first ester group is coupled to remaining Nitrogen atoms in the cyclic compounds. In other preferred embodiments, tertiary amine is selected from a group of cyclic compounds consisting of: 1,4,7, triazacyclononane 1,4 diester 7 monocarboxylate; 1,4,7,10 tetraazacyclododecane 1,4,7 triester 10 monocarboxylate; and 1,4,7,10,13,16 hexaazacyclooctadecane 1,4,7,10,13 pentaester 16 monocarboxylate. In such embodiments the di-, tri- and pentaester comprise the first ester group and the monocarboxylate comprises the carboxylic acid group. In certain embodiments, for example, the first ester group is tertiary butyl ester and the carboxylic acid group is acetate. In yet other preferred embodiments of the carboxylated active ester produced by the above-described process, the carboxylated active ester is monosubstituted N-hydroxy succinimide DOTA.

Still another preferred embodiment of the carboxylated active ester produced by the above-described process, the tertiary amine is selected from a group of acyclic compounds consisting of: diethyltriamines; triethyltetraamines; and pentaethylhexaamines. In such embodiments, the carboxylic acid group is coupled to any one Nitrogen atom in the acyclic compounds and the first ester group is coupled to remaining Nitrogen atoms in the acyclic compounds. In other preferred embodiments, the tertiary amine is selected from a group of acyclic compounds consisting of: diethyltriamine 1,7 diester 4 monocarboxylate; triethyltetraamine 1,4,10 triester 7 monocarboxylate; and pentaethylhexaamine 1,4,7,13,16 pentaester 10 monocarboxylate. In such embodiments, the di-, tri- and pentaester comprise the first ester group and the monocarboxylate comprises the carboxylic acid group. In other embodiments, the ester group in the $R^2$ is tertiary butyl ester and the carboxylic acid group is acetic acid.

In other preferred embodiments of the carboxylated active ester produced by the above-described process, $R^2$ group has the general formula: $R^4\text{—}O\text{—}(C\text{=}O)\text{—}(Y)_m\text{—}$. M is between 0 and 20 and Y is a branched or linear organic substituent. $R^4$ includes an organic substituent and $R^4$ is may be selected from a group consisting of: Alkyl groups having 20 carbon atoms or less; Cycloalkyl groups having 20 carbon atoms or less; and Aromatic groups having 20 carbon atoms or less.

In still other preferred embodiments of the carboxylated active ester produced by the above-described process, the coupling agent is an aminium, guanidium or uronium-containing compound. In other embodiments, the active compound is selected from a group consisting of: imide-containing compounds; aryl-containing compounds substituted with electron withdrawing groups; and triazol-containing compounds. In yet other embodiments, the cleaving comprises exposing said $R^2$ groups of said active ester to an acid. In still other preferred embodiments, an isolated yield of the carboxylated active ester from the tertiary amine is greater than about 50 mole percent.

Although the present invention has been described in detail, those skilled in the art should understand that they can make various changes, substitutions and alterations herein without departing from the scope of the invention.

What is claimed is:

1. A carboxylated active ester comprising:
a tertiary amine where said tertiary amine is cyclic having the general formula:

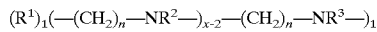

where n is 2 or 3; x is 6 and $R^1$ is $((CH_2)_n\text{—}NR^2\text{—})$ $R^2$ is a substituent that includes a carboxylic acid group having the general formula: H—O—(C=O)—(Y)$_m$— where n is between 1 and 20, and Y is a branched or linear organic substituent, R$^3$ is a substituent that includes an ester group and at least one carbon atom in R$^3$ is attached to any one Nitrogen atom in the tertiary amine and said at least one carbon atom is between said one Nitrogen atom and said ester group, and said R$^2$ is attached to remaining Nitrogen atoms of said tertiary amine.

2. The carboxylated active ester as recited in claim 1, wherein said tertiary amine is a hexaazacyclooctadecane.

3. The carboxylated active ester as recited in claim 1, wherein said tertiary amine is 1,4,7,10,13,16 hexaazacyclooctadecane 1,4,7,10,13 pentacarboxylic acid 16 monoester.

4. The carboxylated active ester as recited in claim 3, wherein said Y is —CH$_2$— and m is 1 and said R$^3$ includes an N-hydroxy succinimide ester group.

* * * * *

UNITED STATES PATENT AND TRADEMARK OFFICE
CERTIFICATE OF CORRECTION

PATENT NO.    : 6,852,854 B1
DATED         : February 8, 2005
INVENTOR(S)   : Zoltan Kovacs, Dhurjati S. Mudigonda and A. Dean Sherry It is certified that error appears in the above-identified patent and that said Letters Patent is hereby corrected as shown below:

Title page,
Item [73], Asssignee, should read -- Board of Regents, The University of Texas System, Austin, Texas (US); Macrocyclics, Dallas, Texas (US) --.

Column 1,
Lines 6-24, should appear as follows:
 -- This application is related to the disclosures of U.S. application Ser. Nos.: 10/262,388, entitled, "IMPROVED PROCESS FOR MAKING A CHELATING AGENT FOR LABELING BIOMOLECULES USING PREFORMED ACTIVE ESTERS;" 10/262.340, entitled, "A PREFORMED ACTIVE ESTER FOR LABELING BIOMOLECULES;" 10/262,335, entitled, "A CHELATING AGENT USING PREFORMED ACTIVE ESTERS FOR LABELING BIOMOLECULES;" 10/262.392, entitled, "A DIAGNOSTIC SYSTEM USING LABELED BIOMOLECULES THAT CONTAIN A CHELATING AGENT FORMED WITH PREFORMED ACTIVE ESTERS;" 10/262,450, entitled, "A THERAPEUTIC SYSTEM USING LABELED BIOMOLECULES THAT CONTAIN A CHELATING AGENT FORMED WITH PREFORMED ACTIVE ESTERS;" all to Zoltan Kovacs; Dhurjati S. Mudigonda; and A. Dean Sherry, all filed on Oct. 1, 2002, commonly assigned with the present invention, and incorporated by reference as if reproduced herein in their entirety.
Lines 49-65, should appear as follows:
 -- There is a longstanding need for the efficient preparation of functionalized chelating agents with active groups that can couple the chelating agent to biomolecules. For example, the efficient functionalization of macrocyclic compounds, such as 1,4,7,10-tetraazocyclododecane-1,4,7,10 tetraacetic acid (DOTA) and 1,4,8,11-tetraazocyclotetradecane 1,4,8,11-tetraacetic acid (TETA), remains problematic. As discussed in U.S. Pat. Nos. 5,428,156 and 5,639,879 to Mease et al., incorporated herein by reference, previous methods for the preparation of functionalized DOTA or TETA are complex, and may yield mixed anhydride products that are highly sensitive to hydrolysis in water, or products with greater than one active ester attached to the chelating agent. The latter can result in the undesirable crosslinking of two or more biomolecules via a reaction between biomolecules and the active esters attached to a single chelating agent. --.

UNITED STATES PATENT AND TRADEMARK OFFICE
CERTIFICATE OF CORRECTION

PATENT NO. : 6,852,854 B1
DATED : February 8, 2005
INVENTOR(S) : Zoltan Kovacs, Dhurjati S. Mudigonda and A. Dean Sherry It is certified that error appears in the above-identified patent and that said Letters Patent is hereby corrected as shown below:

Column 2,
Lines 33-44, should appear as follows:
-- This raises a second problem. Because NHS-substituted DOTA compounds contain a highly reactive Oxygen-Nitrogen bond that links DOTA to NHS, it would be difficult to isolate mono-substituted DOTA-NHS from a mixture of di-, tri- and tetra-NHS substituted DOTA compounds. It is also expected that standard isolation techniques would cause substantial hydrolysis of mono-substituted DOTA-NHS back to the starting compounds. Alternatively, the use of unpurified mixtures of mono-, di-, tri- and tetra-NHS substituted DOTA is expected to result in poor yields of DOTA bioconjugated to biomolecules in useful fashion. --.

Column 4,
Lines 25-42, should appear as follows:
-- The tertiary amine may be any cyclic on acyclic organic compound containing a tertiary amine and having the above-described general formula. Preferred embodiments of cyclic tertiary amines are triazacyclononanes, tetraazacyclododecanes, and hexaazacyclooctadecanes. In such embodiments the carboxylic acid group is coupled to any one Nitrogen atom in the cyclic compound and the first ester group is coupled to remaining Nitrogen atoms in the cyclic compound. More preferably, the tertiary amine is selected from a group of cyclic compounds consisting of: 1,4,7, triazacyclononane 1,4 diester 7 monocarboxylate; 1,4,7,10 tetraazacyclododecane 1,4,7 triester 10 monocarboxylate; and 1,4,7,10,13,16 hexaazacyclooctadecane 1,4,7,10,13 pentaester 16 monocarboxylate. In these embodiments, the di-, tri- and pentaester comprise the first ester group and the monocarboxylate comprises said carboxylic acid group. Even more preferably the first ester group is tertiary butyl ester and the carboxylic acid group is acetate. --.

Column 5,
Lines 38-51, should appear as follows:
-- The coupling agent may comprise any conventional compound known by those skilled in the art to facilitate the coupling of the active compound, such as NHS, to the carboxylate group of R3. In particular, peptide coupling agents, such as those described in Larry Yet, Peptide Coupling Reagent: Names, Acronyms and References, ALBANY MOLECULAR RESEARCH, INC. TECHNICAL REPORT, VOL. 4 NUMBER 1 (1999); or in Louis A. Carpino et al., The Uronium/Guanidium Peptide Coupling Reagents: Finally the True Uronium Salts, ANGEW. CHEM INT. ED. 41,441 (2002), both incorporated by reference herein, may be used. Such compounds are well known to those skilled in the art and may include carbodiimides, such as 1,3-diccyclohexylcarbodiimides (DCC). --.

UNITED STATES PATENT AND TRADEMARK OFFICE
CERTIFICATE OF CORRECTION

PATENT NO. : 6,852,854 B1
DATED : February 8, 2005
INVENTOR(S) : Zoltan Kovacs, Dhurjati S. Mudigonda and A. Dean Sherry It is certified that error appears in the above-identified patent and that said Letters Patent is hereby corrected as shown below:

Column 9,
Lines 10-39, should appear as follows:
-- In certain preferred embodimnents of carboxylated active ester tertiary amine is selected from a group of cyclic compounds consisting of: triazacyclononanes and hexaazacyclooctadecanes. In such embodiments, the ester group is coupled to any one Nitrogen atom in the cyclic compounds and the carboxylic acid group is coupled to remaining Nitrogen atoms in the cyclic compounds. In other preferred embodiments, tertiary amine is selected from a group of cyclic compounds consisting of: 1,4,7, triazacyclononane 1,4 dicarboxylate 7 monoester; and 1,4,7,10,13,16 hexaazacyclooctadecane 1,4,7,10,13 pentacatrboxylate 16 monoester. In such embodiments, the di- and pentacarboxylate comprise the carboxylic acid group in the R.sup.2 and the monoester group comprises the ester group in the R.sup.3. In certain embodiments, for example, carboxylic acid in said R.sup.3 is acetate and said ester group in said R.sup.3 includes N-hydroxy succinimide. In yet other preferred embodiments of the carboxylated active ester, the tertiary amine is selected from a group of acyclic compounds consisting of: diethyltriamines; triethyltetraamines; and pentaethylhexaamines. In such embodiments the ester group is coupled to any one Nitrogen atom in the acyclic compounds and the carboxylic acid group is coupled to remaining Nitrogen atoms in the acyclic compounds. In yet other preferred embodiments, the tertiary amine is selected from a group of acyclic compounds consisting of: triethyltetraamine 1,4,10 tricarboxylate 7 monoester; and pentaethylhexaamine 1,4,7,13,16 pentacarboxylate 10 monoester. In such embodiments, the di-, tri- and pentacarboxylate comprise the carboxylic acid group in the R.sup.2 and the monoester comprises the ester group in the R.sup.3. --.
Lines 64-67, through Column 10, lines 1-17, should appear as follows:
-- In certain preferred embodiments of the carboxylated active ester produced by the above-described process, tertiary amine is selected from a group of cyclic compounds consisting of: triazaccyclononanes, tetraazacyclododecanes; and hexaazacyclooctadecanes. In such embodiments, the carboxylic acid group is coupled to any one Nitrogen atom in the cyclic compounds and the first ester group is coupled to remaining Nitrogen atoms in the cyclic compounds. In other preferred embodiments, tertiary amine is selected from a group of cyclic compounds consisting of: 1,4,7, triazacyclononane 1,4 diester 7 monocarboxylate; 1,4,7,10 tetraazacyclododecane 1,4,7 triester 10 monocarboxylate; and 1,4,7,10,13,16 hexaazacyclooctadecane 1,4,7,10,13 pentaester 16 monocarboxylate. In such embodiments the di-, tri- and pentaester comprise the first ester group and the monocarboxylate comprises the carboxylic acid group. In certain embodiments, for example, the first ester group is tertiary butyl ester and the carboxylic acid group is acetate. In yet other preferred embodiments of the carboxylated active ester produced by the above-described process, the carboxylated active ester is monosubstituted N-hydroxy succinimide DOTA. --.

UNITED STATES PATENT AND TRADEMARK OFFICE
CERTIFICATE OF CORRECTION

PATENT NO. : 6,852,854 B1
DATED : February 8, 2005
INVENTOR(S) : Zoltan Kovacs, Dhurjati S. Mudigonda and A. Dean Sherry It is certified that error appears in the above-identified patent and that said Letters Patent is hereby corrected as shown below:

Column 10,
Line 61, Claim 1 should appear as follows:
1. A carboxylated active ester comprising:
a tertiary amine where said tertiary amine is cyclic having the general formula:
$$(R^1)_1(-(CH_2)_n-NR^2-)_{x-2}-(CH_2)_n-NR^3-)_1$$
where n is 2 or 3; x is 6 and $R^1$ is $((CH_2)_n-NR^2-)$ $R^2$ is a substituent that includes a carboxylic acid group having the general formula: $H-O-(C=O)-(Y)_m$-where m is between 1 and 20, and Y is a branched or linear organic substituent; $R^3$ is a substituent that includes an ester group and at least one carbon atom in $R^3$ is attached to any one Nitrogen atom in the tertiary amine and said at least one carbon atom is between said one Nitrogen atom said ester group, and said $R^2$ is attached to remaining Nitrogen atoms of said tertiary amine. --.

Signed and Sealed this

Fourteenth Day of February, 2006

JON W. DUDAS
*Director of the United States Patent and Trademark Office*